United States Patent
Keskar et al.

(10) Patent No.: US 11,775,665 B2
(45) Date of Patent: Oct. 3, 2023

(54) SYSTEM AND METHOD FOR EXECUTING ACCESS TRANSACTIONS OF DOCUMENTS RELATED TO DRUG DISCOVERY

(71) Applicant: Innoplexus AG, Eschborn (DE)

(72) Inventors: Abhijit Keskar, Pune (IN); Akshesh Doshi, Udiapur (IN)

(73) Assignee: Innoplexus AG, Eschborn (DE)

( * ) Notice: Subject to any disclaimer, the term of this patent is extended or adjusted under 35 U.S.C. 154(b) by 401 days.

(21) Appl. No.: 16/565,592

(22) Filed: Sep. 10, 2019

(65) Prior Publication Data

US 2020/0004771 A1  Jan. 2, 2020

Related U.S. Application Data

(63) Continuation of application No. 16/011,045, filed on Jun. 18, 2018, now Pat. No. 10,452,699.
(Continued)

(51) Int. Cl.
*G06F 16/00* (2019.01)
*G06F 21/62* (2013.01)
(Continued)

(52) U.S. Cl.
CPC ........ *G06F 21/6218* (2013.01); *G06F 16/332* (2019.01); *G06F 16/345* (2019.01);
(Continued)

(58) Field of Classification Search
CPC ...... G06F 16/345; G06F 16/332; G06F 16/93; G06F 21/6209; G06F 21/64;
(Continued)

(56) References Cited

U.S. PATENT DOCUMENTS

| 10,380,195 B1* | 8/2019 | Zelenov | G06F 16/93 |
| 2008/0140616 A1* | 6/2008 | Encina | G06F 16/31 |

(Continued)

OTHER PUBLICATIONS

Non Final Office Action issued in U.S. Appl. No. 16/011,045 dated Nov. 19, 2018, 11 pages.

*Primary Examiner* — Paul Kim
(74) *Attorney, Agent, or Firm* — ZIEGLER IP LAW GROUP, LLC

(57) ABSTRACT

Disclosed is a system for executing access transactions of documents, for example, pertaining to drug discovery. A document and its metainformation are obtained, and value features are extracted from the document based on identification of concepts associated with the document. An importance score of the document is determined based on the value features and the metainformation. A summarized view of the document is constructed based on the value features, the metainformation, the concepts and the importance score. A unique identifier is generated for the document and associated with the summarized view and the concepts of the document. A search query is processed, and the summarized view of the document is retrieved and displayed based on the query. A request for accessing the document is validated, and document access is allowed when the request is validated successfully. The document access transaction may, for example, be facilitated using a blockchain platform.

16 Claims, 8 Drawing Sheets

Related U.S. Application Data

(60) Provisional application No. 62/664,458, filed on Apr. 30, 2018.

(51) Int. Cl.
  *G16H 70/40* (2018.01)
  *H04L 9/06* (2006.01)
  *G06F 16/34* (2019.01)
  *G06F 16/332* (2019.01)
  *G06F 18/21* (2023.01)
  *G06V 30/40* (2022.01)
  *G06F 16/93* (2019.01)

(52) U.S. Cl.
  CPC .......... *G06F 18/21* (2023.01); *G06F 21/6209* (2013.01); *G06V 30/40* (2022.01); *G16H 70/40* (2018.01); *H04L 9/0637* (2013.01); *G06F 16/93* (2019.01)

(58) Field of Classification Search
  CPC .............. G06F 21/6218; G06K 9/6217; G06K 9/00442; G16H 70/40; G06Q 10/10; H04L 9/0637; H04L 2209/38; H04L 9/3228; H04L 9/3239; H04L 9/3297
  See application file for complete search history.

(56) References Cited

U.S. PATENT DOCUMENTS

| | | | |
|---|---|---|---|
| 2017/0277668 A1* | 9/2017 | Luo | G06F 16/345 |
| 2018/0060325 A1* | 3/2018 | Taylor | G06F 16/2228 |
| 2018/0294957 A1 | 10/2018 | O'Brien et al. | |
| 2018/0300315 A1* | 10/2018 | Leal | G06F 16/355 |
| 2020/0099534 A1* | 3/2020 | Lowagie | G06F 21/64 |
| 2020/0257712 A1* | 8/2020 | Singh | G06F 16/3344 |
| 2020/0380090 A1* | 12/2020 | Marion | H04L 9/3239 |

* cited by examiner

Information Required

- Researcher(s)
- Research Field
- Department
- Stage Relevance
- Statistical Significance
- Experiment Type
- Protocol Used
- Technique Used
- Materials Used
- Highlights Summary Keywords OK    Cancel

FIG. 4A

Submit New Documents

| Document | Purpose |
|---|---|
| Summary Report.pdf | |
| Graph.xls | |
| Shelx.jpg | |

OK  Cancel

FIG. 4B

View Details

Long term effect of peripheral lipopolysaccharide in neonatal rats on inflammation and antioxidant parameters in brain Muller, Andy; Andreas, R. (Univ. Of Gothenburg, Sweden)

Jan 23rd, 2017

Type of Experiment: in-vivo brain

Stage Relevance: Pre-clinical

Materials Used: lipopolysaccharide

Summary:
This experiment was carried out in vivo to check if IL1b mRNA did not show any change in Cortex and Hippocampi. All LPS-induced changes were restored in 70 day old rats. 5 PUPs were treated with Saline and LPS (i.p. 2mg/kg). mRNA level of pro-inflammatory cytokine (1L 1b) was examined. Found that 1L 1b mRNA was left significantly unregulated in Substantia nigra. Further experiments like WB, ELISA were also conducted.

Concepts of the document:
LPS, mRNA level, cytokine, Substantia nigra

FIG. 5B

SYSTEM AND METHOD FOR EXECUTING ACCESS TRANSACTIONS OF DOCUMENTS RELATED TO DRUG DISCOVERY

CROSS-REFERENCE TO RELATED APPLICATIONS

This is a continuation patent application of U.S. patent application Ser. No. 16/011,045, filed on Jun. 18, 2018. This application also claims benefit of U.S. Provisional application Ser. No. 62/664,458 as filed on Apr. 30, 2018 and claims priority under 35 U.S.C. 199(e).

TECHNICAL FIELD

The present disclosure relates generally to systems for processing documents pertaining to a research field, and more specifically, to systems for executing access transactions of documents, for example, pertaining to drug discovery. Moreover, the present disclosure relates to methods of executing access transactions of documents.

BACKGROUND

In past few decades, a lot of work such as research, discovery and innovation has been done in various fields of technology. It is desired that findings of such researches, discoveries and innovations be shared among the research community for a progressive development in respective fields thereof. Sometimes, the findings of researches, discoveries and innovations are published by their authors in a form of articles, theses, journals, research papers and so forth. At other times, research organizations end up doing experiments that have been already done by some other research organizations (or personnel). The research organizations are unaware of such experiments, as findings of these experiments are not published, and therefore, are not available in the public domain. Typically, an experiment does not get published, when one of the following happens:
- the experiment has failed to prove a hypothesis, that is, the hypothesis is proven to be false,
- the direction of a research organization (where the experiment was performed) has changed, post the experiment, or
- the experiment has been done in an academic setting (for example, for a doctorate thesis).

In order to create synergy among the research community, exchange of unpublished documents/findings of experiments needs to be facilitated in an easy to use, yet secured manner.

Conventionally, digital platforms (like Elsevier®) provide access to published documents on a subscription-basis. However, such platforms only deal with the published documents, but do not deal with unpublished documents. Currently, even if some research organization (or personnel) is interested in sharing the unpublished experimental findings with others, there is no real-time mechanism for secured exchange and fair valuation of technical documents.

Moreover, authors are reluctant in sharing their unpublished documents on such digital platforms for several reasons. Conventionally, the documents are stored at the digital platforms for sharing them further with interested consumers (for example, such as other research organizations). Consequently, the conventional digital platforms suffer with a risk of data misuse, data theft and other threats caused due to lack of security. Additionally, conventional digital platforms do not authenticate and validate users uploading new documents, and therefore, are incapable of preventing plagiarism. Moreover, upon publishing the documents on the conventional digital platforms, the authors do not have any control over how the documents are shared and with whom they are shared.

Therefore, in light of the foregoing discussion, there exists a need to overcome the aforementioned drawbacks associated with the conventional digital platforms for executing access transaction of the document.

SUMMARY

The present disclosure seeks to provide a system for executing a document access transaction. The present disclosure also seeks to provide a method of executing a document access transaction. The present disclosure seeks to provide a solution to the existing problem of security risks associated with access transaction of documents. An aim of the present disclosure is to provide a solution that overcomes at least partially the problems encountered in prior art, and provides a reliable and secure platform for executing access transaction of the document, thereby eliminating risks pertaining to the security of the document.

In one aspect, an embodiment of the present disclosure provides a system for access transaction of a document containing sensitive and confidential information, the system comprising a server arrangement including one or more processors, the server arrangement being communicably coupled via one or more data communication networks with a first client device and a second client device, wherein the server arrangement, when operated, provides a platform configured to:
- receive an access request for a document selected, by the second user, from a list of documents retrieved in response to a search query and displayed, on a user interface connected to the second client device, wherein each of the document in the list is associated with a summarized view and an importance score, and wherein the importance score, displayed along-with the summarized view, for each of the document in the list is determined on the platform without storing, on the platform, any document of said list of documents;
- validate the access request for the document by the second user;
- retrieve and deliver to the second client device a hash pertaining to the document wherein the hash corresponds to a location of the document in a distributed file storage system;
- cause the first client device to communicate the document to the second client device in response to a successful validation of the access request.

In another aspect, an embodiment of the present disclosure provides a method for access transaction of a document containing sensitive and confidential information, wherein the method is implemented via a system comprising a server arrangement including one or more processors, the server arrangement being communicably coupled via one or more data communication networks with a first client device and a second client device, the method comprising:
- receive an access request for a document selected, by the second user, from a list of documents retrieved in response to a search query and displayed, on a user interface connected to the second client device, wherein each of the document in the list is associated with a summarized view and an importance score, and wherein the importance score, displayed along-with the summarized view, for each of the document in the list is determined on the platform without storing, on the platform, any document of said list of documents;

validating the access request for the document by the second user;

retrieving and delivering to the second client device a hash pertaining to the document wherein the hash corresponds to a location of the document in a distributed file storage system;

causing the first client device to communicate the document to the second client device in response to a successful validation of the access request.

Embodiments of the present disclosure substantially eliminate or at least partially address the aforementioned problems in the prior art, and enable access transaction of the document in a secure environment.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, like elements have been indicated by identical numbers.

Embodiments of the present disclosure will now be described, by way of example only, with reference to the following diagrams wherein:

FIGS. 4A and 4B are example views of a graphical user interface that are presented to a user of a first client device, in accordance with an embodiment of the present disclosure; and FIGS. 5A and 5B are example views of a graphical user interface that are presented to a user of a second client device, in accordance with an embodiment of the present disclosure.

Figure 1:
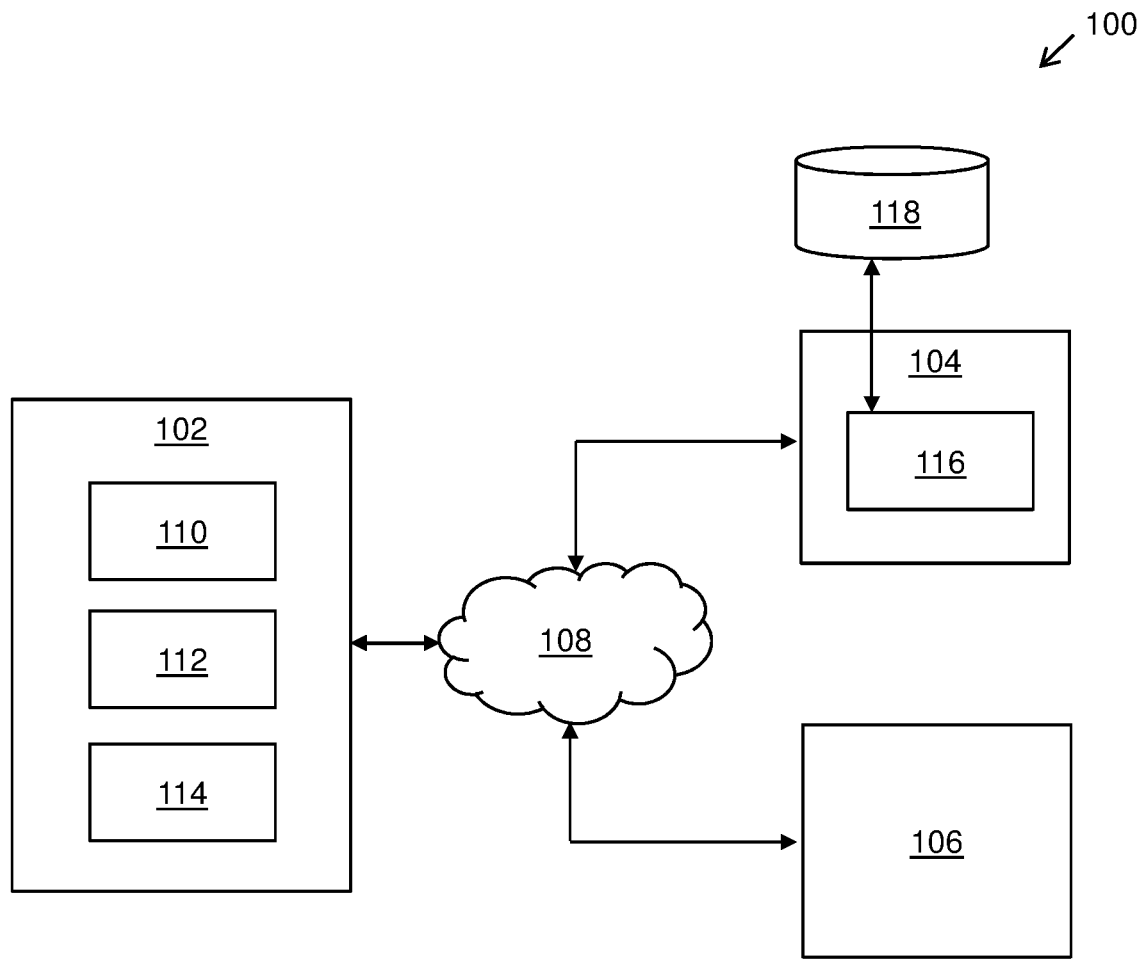
FIG. 1 is a schematic illustration of a network environment, wherein a system for executing a document access transaction is implemented, pursuant to an embodiment of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

In one aspect, an embodiment of the present disclosure provides a system for access transaction of a document containing sensitive and confidential information, the system comprising a server arrangement including one or more processors, the server arrangement being communicably coupled via one or more data communication networks with a first client device and a second client device, wherein the server arrangement, when operated, provides a platform configured to:

receive an access request for a document selected, by the second user, from a list of documents retrieved in response to a search query and displayed, on a user interface connected to the second client device, wherein each of the document in the list is associated with a summarized view and an importance score, and wherein the importance score, displayed along-with the summarized view, for each of the document in the list is determined on the platform without storing, on the platform, any document of said list of documents;

validate the access request for the document by the second user;

retrieve and deliver to the second client device a hash pertaining to the document wherein the hash corresponds to a location of the document in a distributed file storage system;

cause the first client device to communicate the document to the second client device in response to a successful validation of the access request.

In another aspect, an embodiment of the present disclosure provides a method for access transaction of a document containing sensitive and confidential information, wherein the method is implemented via a system comprising a server arrangement including one or more processors, the server arrangement being communicably coupled via one or more data communication networks with a first client device and a second client device, the method comprising:

receive an access request for a document selected, by the second user, from a list of documents retrieved in response to a search query and displayed, on a user interface connected to the second client device, wherein each of the document in the list is associated with a summarized view and an importance score, and wherein the importance score, displayed along-with the summarized view, for each of the document in the list is determined on the platform without storing, on the platform, any document of said list of documents;

validating the access request for the document by the second user;

retrieving and delivering to the second client device a hash pertaining to the document wherein the hash corresponds to a location of the document in a distributed file storage system;

causing the first client device to communicate the document to the second client device in response to a successful validation of the access request.

The aforesaid system for executing the document access transaction and the aforesaid method of executing the document access transaction as described in the present disclosure provide a single platform for executing the document access transaction in a secure and reliable manner. Pursuant to embodiments of the present disclosure, the server arrangement of the aforesaid system neither stores a copy of the document locally nor stores it in a database. This potentially prevents any fraudulent activity, for example, such as a misuse of the document by unauthorized parties. In other words, the aforesaid system and method reduce the risk of data misuse, data theft and other threats that are often caused due to a lack of security in conventional digital platforms.

Moreover, the aforesaid server arrangement is configured to present (namely, display) only the summarized view of the document, namely brief information associated with the document, before a rightful access to the document is provided to an authorized party. In other words, the access to the document (for example, a document containing highly sensitive and confidential information) is not provided, unless the request from the second client device is validated successfully.

It will be appreciated that the aforesaid system and the aforesaid method are not limited to execute document access transaction for only a single document. The system and method can be employed to execute document access transaction for multiple documents at a given time. The multiple documents could comprise documents owned by a same first client device or documents owned by different first client devices.

Optionally, the aforementioned document is related to a current research work performed in a research organization. Throughout the present disclosure, the term "document" refers to a set of files in which an observation made in a scientific investigation or experiment is recorded, wherein the observation can be recorded in a form of one or more types of data. Some examples of various types of data are text data, tabular data, image data, video data and audio data. Thus, files can be in any suitable file formats depending upon the type of data that is stored therein. As an example, the set of files could comprise a single file having one or more of: a written text, one or more tables, one or more graphs, or a set of images. As another example, the set of files could comprise a plurality of files having different types of data, for example, such as a written text, one or more tables, one or more graphs, a set of images, one or more videos, or one or more audio clips.

Throughout the present disclosure, the term "server arrangement" refers to an arrangement of one or more servers that includes one or more processors configured to perform various operations, for example, as mentioned earlier. Optionally, the server arrangement includes any arrangement of physical or virtual computational entities capable of performing the various operations. The term "one or more processors" may refer to one or more individual processors, processing devices and various elements associated with a processing device that may be shared by other processing devices. Additionally, the one or more individual processors, processing devices and elements are arranged in various architectures for responding to and processing the instructions that drive the aforesaid system.

Moreover, it will be appreciated that the server arrangement can be implemented by way of a single hardware server. The server arrangement can alternatively be implemented by way of a plurality of hardware servers operating in a parallel or distributed architecture. As an example, the server arrangement may include components such as memory, a processor, a network adapter and the like, to store and process information pertaining to the document and to communicate the processed information to other computing components, for example, such as a client device.

Throughout the present disclosure, the term "server" generally refers to a device executing an application, program, or process in a client/server relationship that responds to requests for information or services by another application, program, process or device (namely, a client) on a data communication network. Optionally, a given server is implemented by way of a device executing a computer program that provides various services (for example, such as a database service) to other devices, modules or apparatus.

The term "client device" generally refers to a device executing an application, program, or process in a client/server relationship that requests information or services from another application, program, process or device (namely, a server) on a data communication network. Importantly, the terms "client" and "server" are relative, as an application may be a client to one application but a server to another application.

Notably, the first and second client devices are configured to function as a "client" in a client/server relationship with the server arrangement. However, the first and second client devices may be configured to function as a "server" in a client/server relationship with other computing devices. Throughout the present disclosure, the terms "first client device" and "second client device" refer to devices associated with a first user and a second user that acts as clients to the server arrangement in a client/server relationship, wherein such devices can be personal devices or servers in local environments of the first user and the second user, respectively. As an example, the first client device can be an internal server of the research organization where the current research work has been performed (namely, from where the document has originated), while the second client device can be an internal server of another research organization that is interested in accessing the document.

It will be appreciated that the document may have been authored or co-authored by one or more authors. The first user can be any one of the one or more authors, a representative of the one or more authors, or an owner of the document, who uses the first client device to perform commercial transactions of the document (for example, such as sale, licensing and so forth). On the other hand, the second user can be, for example, an individual or a representative of a group of individuals or an organization seeking access to the document, wherein the second user uses the second client device to perform commercial actions (for example, such as purchase, lease, rent, and so forth) for consuming the document.

Throughout the present disclosure, the term "remote extraction module" refers to a module comprising programmable components that is stored on the first client device. Optionally, the remote extraction module is implemented by way of a trusted software application that, when executed at the first client device, obtains the document and the metainformation pertaining to the document. Optionally, in such a case, the trusted software application is received (for example, downloaded) from the server arrangement or a trusted third party. The trusted third party can be a publicly-accessible digital distribution platform, for example, such as Google Play®, the App Store® (for iOS®) and the like.

Pursuant to embodiments of the present disclosure, when triggered, the remote extraction module is configured to present a graphical user interface to the first user that allows the first user to submit to the remote extraction module the document and the metainformation pertaining to the document. Optionally, the metainformation pertaining to the document is submitted in a form of a meta file.

Optionally, in order to submit the metainformation, the remote extraction module is configured to provide the first user with a form having input fields, via the graphical user interface. The first user is required to fill the form to provide the metainformation pertaining to the document. Optionally, the remote extraction module is configured to collate the metainformation pertaining to the document into the meta file.

Optionally, the metainformation pertaining to the document comprises information about one or more of: names of the one or more authors, name of a research organization where the current research work has been performed, a statistical significance of the current research work, a set of keywords associated with the current research work, one or more research fields to which the current research work pertains, a hypothesis of the current research work, an experiment performed during the current research work, a stage of drug development to which the current research work is applicable. Additionally, optionally, the metainformation also comprises information pertaining to cost incurred in the current research work of the one or more authors.

Optionally, the remote extraction module is configured to allow, via the graphical user interface, the first user to view and edit the metainformation previously submitted by the first user.

Moreover, optionally, the remote extraction module is configured to provide the first user, via a graphical user interface of the first client device, with a Single Sign-On (SSO) feature, based on stored credentials of the first user. Optionally, the graphical user interface of the first client device allows the first user to input his/her credentials (for example, a user identification and a password) to complete a sign-in procedure. Additionally, optionally, the graphical user interface of the first client device allows the first user to store such credentials on the first client device, thereby allowing the first user to sign-in without a need to input the credentials.

Beneficially, the server arrangement is configured to authenticate the first user prior to allowing the first user to submit the document. This potentially prevents an unauthorized party from masquerading as the first user.

Optionally, when signing-up for the first time, the first user is required to provide one-time information, for example, including information about the one or more authors. Optionally, the information about the one or more authors is indicative of at least one of: names or unique identifiers of the one or more authors, academic qualifications of the one or more authors, academic institutes from where the one or more authors obtained the academic qualifications, research organizations and/or departments to which the one or more authors are currently affiliated, areas of expertise of the one or more authors, areas of interest of the one or more authors, digital libraries where the one or more authors have made publications.

Optionally, the remote extraction module is configured to communicate the information about the one or more authors to the server arrangement, wherein the information about the one or more authors is to be utilized by the scoring module of the server arrangement. More optionally, the information about the one or more authors is communicated to the server arrangement during an initial sign-up procedure.

Furthermore, optionally, the remote extraction module is configured to convert a data format of the document into a predefined data format prior to extracting the one or more value features from the document. Optionally, the predefined data format is a file format, for example, such as a JavaScript Object Notation (JSON) format. It will be appreciated that the document obtained from the first client device can be in any file format, for example, such as a Portable Document Format (PDF), Joint Photographic Experts Group (JPEG) format, Microsoft Word document format, Microsoft Excel worksheet format and so forth.

Pursuant to embodiments of the present disclosure, the remote extraction module is configured to process the document to extract the one or more value features therefrom. Optionally, when processing the document, different sections of the document are identified and at least one of the sections of the document is further processed to extract the one or more value features, wherein the one or more value features are indicative of entities and semantic inter-relationships between the entities as mentioned in the at least one of the sections of the document.

Optionally, the document is related to a current research work of one or more authors, and wherein the one or more value features of the document comprise information elements indicative of entities and semantic inter-relationships between the entities. Beneficially, a semantic inter-relationship between two given entities is indicative of a causal relationship between the two given entities. As an example, in drug discovery, examples of a causal relationship between a drug and a disease could be "causes", "inhibits", "catalyzes" and so on.

Optionally, the remote extraction module is configured to compare words (and/or phrases) occurring in the at least one of the sections of the document with the concepts stored in the ontological databank, and to identify the one or more concepts of the document based on the comparison with the concepts stored in the ontological databank. Optionally, in this regard, the remote extraction module is configured to stem the words prior to performing said comparison, and identify words matching the concepts stored in the ontological databank as the one or more concepts of the document.

Optionally, sentences present in the at least one of the sections of the document are processed by employing a frame semantic parsing technique to generate semantic frames, wherein these semantic frames form a part of the one or more value features. Optionally, the frame semantic parsing technique employs a directed acyclic transition-based recurrent neural network.

In the frame semantic parsing technique, sentences or phrases in a natural language are parsed and processed to generate the semantic frames. In other words, lexical targets (namely, words and phrases) in their sentential contexts are processed to generate the semantic frames. Herein, the term "semantic frame" refers to a coherent structure of related concepts that specify features that are typically associated with a particular word (for example, attributes, functions and interactions of a particular entity). As an example, a semantic frame observed in research work related to drug discovery could include at least two of: a drug, a pathway, a target, a disease.

Such a frame semantic parsing technique is optionally implemented using known techniques and models, for example as described in a published paper, titled "SLING: A framework for frame semantic parsing" (Michael Ringgaard et. al., available here https://arxiv.org/abs/1710.07032).

Beneficially, the frame semantic parsing technique employs the aforementioned ontological databank. It will be appreciated that the frame semantic parsing technique identifies the entities and their semantic inter-relationships even when the entities and their semantic inter-relationships may be defined very subjectively in the document.

Throughout the present disclosure, the term "ontological databank" refers to a data repository that is configured to store information about a set of concepts related to a technical field (namely, a subject area, a technical domain and so forth), wherein said information is indicative of types of concepts, properties of the concepts and semantic inter-relationships between the concepts. Optionally, the ontological databank is configured to store the information about the set of concepts in a structured manner. Additionally, optionally, the ontological databank is configured to store information on how a certain concept in a certain technical field may be associated with one or more concepts in other field(s).

In an embodiment, the ontological databank is stored at the first client device. In another embodiment, the ontological databank is stored at a database arrangement associated with the server arrangement. Optionally, the database arrangement comprises one or more databases.

For illustration purposes only, there will now be considered an example document related to drug discovery, wherein an abstract of the document is as follows:

"This experiment was carried out in vivo to check if IL1b mRNA did not show any change in Cortex and Hippocampi. All LPS-induced changes were restored in 70 day old rats. 5 PUPs were treated with Saline and LPS (IP 2 mg/kg). mRNA level of pro-inflammatory cytokine (IL1b) was examined. Found that ILib mRNA was left significantly unregulated in Substantia nigra. Further experiments like WB, ELISA were also conducted."

In such a case, the abstract of the example document is processed, by employing an ontological databank related to drug discovery, to extract value features indicative of entities and their semantic inter-relationships, wherein the entities and their types can be identified as follows:
  Drug: LPS
  Disease: pro-inflammatory cytokine
  Target: Cortex and Hippocampi
Moreover, the semantic inter-relationships can be represented as follows:
LPS—No Effect—Cytokine Moreover, optionally, upon receiving the one or more value features and the metainformation pertaining to the document, the server arrangement is configured to process the one or more value features and the metainformation to check the authenticity of the document. This potentially prevents a fraudulent user or the first user from uploading a facsimile of the document intentionally or ignorantly, thereby preventing plagiarism and identity theft.

Pursuant to embodiments of the present disclosure, the scoring module of the server arrangement, in operation, determines the importance score of the document based on the one or more value features and the metainformation pertaining to the document and optionally, the aforementioned information about the one or more authors.

Optionally, the scoring module is configured to access, based upon the information about the one or more authors, information indicative of entities and semantic inter-relationships specific to a previous research work of the one or more authors. Optionally, in this regard, the scoring module is configured to:
  obtain, from a plurality of database servers, other documents authored by at least one of the one or more authors;
  process the other documents to identify the entities and the semantic inter-relationships specific to the previous research work; and
  store the information indicative of the entities and the semantic inter-relationships specific to the previous research work.

Hereinabove, the term "database servers" refers to database servers related to a plurality of digital libraries that publish technical documents authored by various authors or research organizations, while the term "other documents" refers to all the documents authored or co-authored previously (namely, prior to the current research work) by the at least one of the one or more authors that are available in the public domain, and therefore, represent the previous research work of the one or more authors. Such published technical documents may, for example, be pre-clinical reports, clinical reports, scientific articles, theses, granted patents, published patent applications and so on.

Optionally, in order to obtain the other documents, the plurality of database servers are queried using the names or other unique identifiers of the one or more authors (as obtained from the information about the one or more authors).

Optionally, when processing a given other document, different sections of the given other document are identified and at least one of the different sections of the given other document is further processed to identify the entities and the semantic inter-relationships specific to the previous research work. It will be appreciated that technical documents typically have well-defined sections that can be identified from their respective headings, and therefore, it is possible to select at least one of these sections for further processing. As an example, a scientific report related to an experiment may include various sections having suitable headings, for example, such as 'Abstract', 'Introduction', 'Materials and Methods', 'Results', 'Discussion', 'Conclusion' and 'References'. In such a case, the section(s) 'Abstract' and/or 'Conclusion' may be further processed to identify entities and semantic inter-relationships mentioned in the scientific report. As another example, a patent document typically includes sections having headings, for example, such as 'Abstract', 'Background', 'Summary', 'Brief Description of Drawings', 'Detailed Description' and 'Claims'. In such a case, the section(s) 'Abstract' and/or 'Claims' may be further processed to identify entities and semantic inter-relationships mentioned in the patent document.

Optionally, the other documents are processed by employing the aforementioned frame semantic parsing technique to generate corresponding semantic frames. Optionally, in such a case, sentences present in at least one section of each of the other documents are parsed and processed to generate the semantic frames. Optionally, these semantic frames form a part of the information indicative of the entities and the semantic inter-relationships specific to the previous research work.

Optionally, the information indicative of the entities and the semantic inter-relationships specific to the previous research work is stored at a data repository of the server arrangement. Optionally, the data repository is implemented by way of data memory associated with at least one of the one or more processors of the server arrangement. Alternatively, optionally, the data repository is implemented by way of the database arrangement associated with the server arrangement.

Optionally, the scoring module is configured to obtain and process the other documents even before the document is obtained by the remote extraction module. It will be appreciated that the other documents can be obtained and processed after the initial sign-up procedure.

Moreover, optionally, the scoring module is configured to process the one or more value features and/or the metainformation pertaining to the document to determine a technical field of the current research work. Optionally, the scoring module is configured to access, based upon the technical field of the current research work, information indicative of entities and semantic inter-relationships related to the technical field. Optionally, in this regard, the scoring module is configured to:
  obtain, from the plurality of database servers, a plurality of documents pertaining to the technical field of the current research work;
  process the plurality of documents to identify the entities and the semantic inter-relationships related to the technical field; and
  store the information indicative of the entities and the semantic inter-relationships related to the technical field.

Optionally, in order to obtain the plurality of documents pertaining to the technical field of the current research work, the plurality of database servers are queried using key words (namely, key strings) that are relevant to the technical field. Hereinabove, the term "database servers" refers to the database servers related to the plurality of digital libraries that publish technical documents authored by various researchers or research organizations, while the term "plurality of documents" refers to all the documents pertaining to the technical field that are available in the public domain, and therefore, represent knowledge available publicly.

Optionally, when processing a given document, different sections of the given document are identified and at least one of the different sections of the given document is further processed to identify the entities and the semantic inter-relationships related to the technical field, as described earlier.

Optionally, the information indicative of the entities and the semantic inter-relationships related to the technical field is stored at the aforementioned data repository or another data repository of the server arrangement.

Optionally, the scoring module is configured to obtain and process the plurality of documents even before the aforementioned document is obtained by the remote extraction module. Optionally, the plurality of documents are obtained and processed for a plurality of technical fields; for each technical field, information indicative of entities and semantic inter-relationships related to that technical field is stored at the data repository and updated from time to time.

Optionally, the scoring module is configured to:
  compare the entities and the semantic inter-relationships specific to the current research work with the entities and the semantic inter-relationships related to the technical field of the current research work;
  compare the entities and the semantic inter-relationships specific to the current research work with the entities and the semantic inter-relationships specific to the previous research work of one or more authors; and
  determine the importance score based upon said comparisons.

Optionally, in this regard, the scoring module is configured to:
  generate a current-work graph representing the entities and the semantic inter-relationships specific to the current research work;
  generate a knowledge graph representing the entities and the semantic inter-relationships related to the technical field of the current research work;
  generate a previous-work graph representing the entities and the semantic inter-relationships specific to the previous research work; and
  perform the aforementioned comparisons using the current-work graph, the previous-work graph and the knowledge graph.

Optionally, the knowledge graph represents the entities and the semantic inter-relationships related to the technical field, and weights assigned to the semantic inter-relationships. Likewise, optionally, the previous-work graph represents the entities and the semantic inter-relationships specific to the previous research work, and weights assigned to the semantic inter-relationships. Similarly, optionally, the current-work graph represents the entities and the semantic inter-relationships specific to the current research work, and weights assigned to the semantic inter-relationships.

Optionally, in this regard, a given graph is generated by linking the entities according to the semantic inter-relationships between them. In the given graph, the entities are represented by nodes of the given graph, while the semantic inter-relationships between the entities are represented by edges (namely, links) between the nodes.

As mentioned above, the semantic inter-relationships between the entities have weights assigned thereto. Optionally, in case of the previous-work graph, a given semantic inter-relationship between two entities is assigned a weight based upon at least one of: a type of causal relationship represented by the given semantic inter-relationship between the two entities, the number of documents authored by the at least one of the one or more authors in which the given semantic inter-relationship occurred, ranks of digital libraries where the documents were published.

Likewise, optionally, in case of the knowledge graph, a given semantic inter-relationship between two entities is assigned a weight based upon at least one of: a type of causal relationship represented by the semantic inter-relationship between the two entities, the number of documents in which the semantic inter-relationship occurred, ranks of digital libraries where the documents were published.

Moreover, optionally, in case of the current-work graph, a given semantic inter-relationship between two entities is assigned a weight based upon the weight of the given semantic inter-relationship in the knowledge graph.

It will be appreciated that the weight of the given semantic inter-relationship represents a strength of the given semantic inter-relationship.

Furthermore, optionally, the scoring module is configured to:
  process the information about the one or more authors, whilst taking into consideration rankings of the academic institutes, the research organizations and the digital libraries, to determine a reputation factor associated with the document; and
  determine the importance score of the document, based upon the reputation factor.

Moreover, optionally, the scoring module is configured to:
  process the information pertaining to the cost incurred in the current research work to determine a cost factor associated with the document; and determine the importance score of the document, based upon the cost factor.

Furthermore, optionally, the scoring module is configured to:

process the information about the statistical significance of the current research work, whilst taking into account a rank of the research organization where the current research work has been performed, to determine a statistical-significance factor associated with the document; and determine the importance score of the document, based upon the statistical-significance factor.

Throughout the present disclosure, the term "importance score" refers to a rating (namely, a grade or a value) that is determined for the document, wherein the importance score is indicative of a quantified importance of the current research work from a technical point of view. Thus, the importance score can be used to provide a potential consumer with an insight into the current research work, and to help the consumer in deciding whether or not to purchase the document. Moreover, the importance score can be used to provide the first user with a guidance for pricing the document for selling the document to research organizations or personnel that are interested in buying the document.

Moreover, optionally, the importance score is a monetary value. Optionally, the monetary value is in a crypto-currency for enabling future transactions of the document using a blockchain. It will be appreciated that the monetary value can alternatively be in any suitable currency, as required.

As mentioned earlier, the server arrangement is configured to construct the summarized view of the document based on at least one of: the one or more value features, the metainformation, the one or more concepts of the document and the importance score. Notably, the summarized view of the document provides a concise outline of the document representative of significant features of the document. Furthermore, the summarized view of the document provides the second user with a synoptic description of the document.

Optionally, the summarized view comprises a brief description of the document, bibliographical information pertaining to the document, a list of keywords associated with the document, and the importance score of the document. Optionally, the list of keywords associated with the document includes at least one of the one or more concepts of the document. Moreover, optionally, the server arrangement is configured to employ Natural Language Generation (NLG) techniques to generate the brief description of the document based on the one or more concepts of the document.

Furthermore, as mentioned earlier, the persistence module of the server arrangement is configured to generate a unique identifier for the document, and associate the unique identifier with the summarized view and with the one or more concepts of the document. Optionally, the unique identifier is a string of alphabets, numbers, symbols or a combination thereof. Specifically, the unique identifier serves as a means for identification and retrieval of the summarized view of the document (and consequently, the document).

Optionally, the persistence module is configured to store the unique identifier of the document with the summarized view and with the one or more concepts of the document in a non-volatile storage location, for example, such as at least one of the one or more databases of the database arrangement.

Optionally, the unique identifier of the document is stored with the one or more concepts of the document in a form of inverted indices. Optionally, the persistence module is configured to map a given concept to unique identifiers of a plurality of documents in which the given concept is identified. In other words, the given concept acts as an index to the unique identifiers of the plurality of documents in which the given concept is identified.

For illustration purposes only, there will now be considered an example scenario, wherein:

a first document has a unique identifier "B6A34" that is associated with concepts, "Cancer", "Lung Cancer", "EGFR" identified therefrom;

a second document has a unique identifier "C8X45" that is associated with concepts "Cancer", "Breast Cancer", "Lung Cancer" identified therefrom; and a third document has a unique identifier "S3F89" that is associated with concepts "Cancer", "Diabetes" and "EGFR" identifier therefrom.

In the illustrated example, a table below represents the mapping of the concepts to the unique identifiers as follows:

| Concept | Unique Identifier(s) |
| --- | --- |
| Cancer | B6A34, C8X45, S3F89 |
| Lung Cancer | B6A34, C8X45 |
| Breast Cancer | C8X45 |
| EGFR | B6A34, S3F89 |
| Diabetes | S3F89 |

It will be appreciated that such inverted indexing is particularly beneficial when there are a large number of documents (for example, in millions or more), because searching for documents matching a particular concept can be performed relatively fast.

Moreover, as mentioned earlier, the server arrangement is configured to receive the search query from the second client device and process the search query to identify the at least one concept pertaining to the search query. Specifically, the second client device is the device associated with the second user who is interested in accessing the document.

Optionally, the server arrangement is configured to present the graphical user interface to the second user that allows the second user to input the search query. As an example, the second user can provide the search query in an input field displayed on the graphical user interface of the second client device. The search query may, for example, comprise a set of keywords entered by the second based on his/her area of interest.

Optionally, the search query is parsed and compared with the concepts stored in the ontological databank to identify a possible match therebetween. Additionally, optionally, a spell check is performed on the search query.

Optionally, the search query comprises one or more query segments (namely, fragments, phrases and so forth) and contextual (namely, conceptual, semantic and so forth) associations therebetween. A query segment is a part of a search query that has a significant contextual meaning. As an example, the search query can be as follows: "drugs tablets for curing lung cancer". In such a case, the query segments can be as follows: "drugs", "tablets", "curing", "lung", and "cancer". Optionally, the one or more query segments are compared with the concepts stored in the ontological databank to identify the at least one concept pertaining to the search query.

Optionally, the server arrangement is configured to expand the search query to include at least one of: lexical variants for at least one of the one or more query segments, synonyms of at least one of the one or more query segments, abbreviations of at least one of the one or more query segments, word stems of at least one of the one or more query segments. Additionally, optionally, the lexical variants, the synonyms, the abbreviations and/or the word stems are processed into a canonical form (namely, to standardize the one or more query segments).

Moreover, optionally, the server arrangement is configured to convert the search query into a machine-readable format. Optionally, the search query is converted into the JSON format or any other suitable format.

Furthermore, as mentioned earlier, the server arrangement is configured to retrieve the summarized view of the document based on the unique identifier of the document, when the at least one concept pertaining to the search query matches at least one of the one or more concepts of the document. Optionally, in this regard, the at least one concept pertaining to the search query is compared with each of one or more concepts of multiple documents that were associated and stored by the persistence module.

Subsequently, for each concept that is found to match the at least one concept pertaining to the search query, summarized views of all documents whose unique identifiers are associated with that concept are retrieved. As mentioned previously, the unique identifiers of the documents are associated with the summarized views of the documents. Therefore, when the at least concept pertaining to the search query matches the at least one of the one or more concepts of the document, the summarized view of the document is retrieved.

Optionally, the server arrangement is configured to present, via the graphical user interface of the second client device, a list of documents that matched the search query.

Moreover, the server arrangement is configured to display, on the graphical user interface of the second client device, the summarized view of the document. Optionally, in this regard, the summarized view is displayed to the second user, based upon a user's selection of the document from the list of documents. This allows the second user to check whether or not the document is relevant to his/her search query, thereby helping him/her make a decision regarding the document.

It will be appreciated that the summarized view can alternatively be constructed on the fly, when the summarized view is required to be displayed to the second user. In such cases, the summarized view is not pre-stored.

Pursuant to embodiments of the present disclosure, the graphical user interface allows the user to initiate the request for accessing the document. In this regard, the server arrangement is configured to validate the request, received from the second client device for accessing the document, using the validation module of the server arrangement.

Optionally, in this regard, the validation module is configured to validate an identity of the second user and/or a payment transaction made by the second user for accessing the document.

Optionally, upon successful validation, the first client device is configured to allow the second client device to access the document over a data communication network that is different from the one or more data communication networks. As mentioned earlier, the server arrangement is communicably coupled with the first client device and the second client device using the one or more data communication networks. Therefore, allowing the access of the document over the data communication network that is different from the one or more data communication networks ensures security of the document. In an instance, when a security of the one or more data communication networks is compromised, the security of the document may not be breached.

Moreover, it will be appreciated that the scoring module, the persistence module and the validation module can be implemented by way of a single processor or separate processors of the server arrangement.

Furthermore, optionally, a document sharing module stored on the first client device is configured to encrypt the document using a key of the first client device. Optionally, the document sharing module is configured to generate the key to be used for encrypting the document. The document is encrypted to prevent unauthorized access of the document from malicious parties masquerading as the second client device.

Furthermore, the key that is used to encrypt the document may, for example, be a hash function, a mathematical operator, a mathematical operation and so forth.

Optionally, the document sharing module is configured to store the encrypted document in a distributed file system. The distributed file system provides a protocol for storing and exchanging documents for peer-to-peer transfers. Furthermore, the encrypted document is stored at various peer nodes pertaining to various public nodes of the distributed file system. The peer nodes are not dependent on each other; this ensures that the distributed file system has no failures due to non-functionality of any of the peer nodes. Once stored, the content of the encrypted document cannot be changed. This makes the distributed file system secure. An example of the distributed file system is InterPlanetary File System (IPFS).

Optionally, in this regard, the distributed file system is operable to generate a hash that uniquely identifies the document. Optionally, in order to generate the hash of the document, the distributed file system applies a hash operation on a combination of: the encrypted document, metadata of the document and a file format of the document. The hash of the document is a string of alphanumeric characters having a fixed length. It will be appreciated that the length of the string is based upon the hash operation that is applied on the aforesaid combination.

The distributed file system communicates the hash to the document sharing module. Optionally, the document sharing module is configured to communicate the hash of the document to the server arrangement.

Moreover, optionally, the document sharing module is configured to store the hash of the document on a blockchain platform, wherein the blockchain platform associates a timestamp with the hash of the document. Specifically, the blockchain platform relates to a distributed ledger arrangement that is configured to store a list of records. More specifically, in the blockchain platform, each block stores a cryptographic hash of a previous block, new information stored in the block and a timestamp associated with the block. Pursuant to embodiments of the present disclosure, the new information stored in the block comprises the hash of the document.

Furthermore, the blockchain platform is managed by a peer-to-peer network collectively adhering to a protocol for inter-node communication and validating new blocks in a blockchain. Moreover, once a block is stored in the blockchain (namely, the distributed ledger arrangement), the block cannot be altered. Thus, storing the hash of the document in the blockchain platform provides an immutable proof of publishing of the encrypted document with its associated timestamp.

Optionally, the server arrangement is configured to communicate the hash of the document to the second client device, for example, upon receipt or successful validation of the request for accessing the document. This enables the second client device to retrieve the encrypted document from the distributed file system.

Moreover, optionally, the document sharing module is configured to communicate to the second client device a key to be used to decrypt the encrypted document, upon successful validation of the request for accessing the document. This enables the second client device to decrypt the encrypted document using the key.

Furthermore, in some implementations, the second client device is configured to make a payment transaction for purchasing the document using the aforementioned blockchain platform.

For illustration purposes only, there will now be considered an example network environment, wherein a system for executing a document access transaction can be implemented pursuant to embodiments of the present disclosure. One such network environment has been illustrated in conjunction with FIG. 1 as explained in more detail below.

The network environment includes a first client device and a second client device, a server arrangement of the system, a database arrangement of the system, and one or more data communication networks. The server arrangement, comprising one or more processors, is communicably coupled via the one or more data communication networks with the first client device and the second client device. Optionally, the network environment also includes a plurality of database servers communicably coupled via the one or more data communication networks with the one or more processors of the server arrangement.

It will be appreciated that it is not necessary for the one or more processors of the server arrangement to be coupled in communication with all the client devices simultaneously at all times.

The one or more data communication networks can be a collection of individual networks, interconnected with each other and functioning as a single large network. Such individual networks may be wired, wireless, or a combination thereof. Examples of such individual networks include, but are not limited to, Local Area Networks (LANs), Wide Area Networks (WANs), Metropolitan Area Networks (MANs), Wireless LANs (WLANs), Wireless WANs (WWANs), Wireless MANs (WMANs), the Internet, second generation (2G) telecommunication networks, third generation (3G) telecommunication networks, fourth generation (4G) telecommunication networks, fifth generation (5G) telecommunication networks and Worldwide Interoperability for Microwave Access (WiMAX) networks.

Examples of the first and second client devices include, but are not limited to, mobile phones, smart telephones, Mobile Internet Devices (MIDs), tablet computers, Ultra-Mobile Personal Computers (UMPCs), phablet computers, Personal Digital Assistants (PDAs), web pads, Personal Computers (PCs), handheld PCs, laptop computers, desktop computers, large-sized touch screens with embedded PCs, a server, and Network-Attached Storage (NAS) devices.

The one or more processors of the server arrangement are configured to execute machine readable instructions that cause the server arrangement to perform operations, for example, as illustrated with respect to the aforementioned aspect.

Moreover, the present description also relates to the method as described above. The various embodiments and variants disclosed above apply mutatis mutandis to the method.

Optionally, the method further comprises converting a data format of the obtained document, using the remote extraction module, into a predefined data format prior to extracting the one or more value features from the document.

Optionally, the document is related to a current research work of one or more authors, wherein the one or more value features of the document comprise information elements indicative of entities and semantic inter-relationships between the entities specific to the current research work.

Optionally, the method comprises using the scoring module to:
compare the entities and the semantic inter-relationships specific to the current research work with entities and semantic inter-relationships related to a technical field of the current research work;
compare the entities and the semantic inter-relationships specific to the current research work with entities and semantic inter-relationships specific to a previous research work of the one or more authors; and
determine the importance score based upon said comparisons.

Optionally, the method comprises using the scoring module to:
generate a current-work graph representing the entities and the semantic inter-relationships specific to the current research work;
generate a knowledge graph representing the entities and the semantic inter-relationships related to the technical field of the current research work;
generate a previous-work graph representing the entities and the semantic inter-relationships specific to the previous research work; and
perform said comparisons using the current-work graph, the previous-work graph and the knowledge graph.

Optionally, the method comprises mapping a given concept to unique identifiers of a plurality of documents in which the given concept is identified, using the persistence module.

Optionally, the method further comprises providing a user of the first client device, via a graphical user interface of the first client device, with a single sign-on feature based on stored credentials of the user.

More optionally, the method comprises allowing the second client device to access the document over a data communication network that is different from the one or more data communication networks.

Optionally, the method further comprises using a document sharing module stored on the first client device to:
encrypt the document using a key of the first client device; and
store the encrypted document in a distributed file system, wherein the distributed file system is operable to generate a hash that uniquely identifies the document.

Optionally, the method further comprises storing the hash of the document on a blockchain platform, wherein the blockchain platform associates a timestamp with the hash of the document.

DETAILED DESCRIPTION OF THE DRAWINGS

Referring now to the drawings, particularly by their reference numbers, FIG. 1 is a schematic illustration of a network environment 100, wherein a system for executing a document access transaction is implemented, pursuant to an embodiment of the present disclosure. The network environment 100 comprises a server arrangement 102 including one or more processors, a first client device 104 and a second client device 106. The server arrangement 102 is communicably coupled via one or more data communication networks (depicted as a data communication network 108) with the first client device 104 and the second client device 106.

The server arrangement 102 comprises a scoring module 110, a persistence module 112 and a validation module 114. As shown, the first client device 104 comprises a remote extraction module 116. The remote extraction module 116 is communicably coupled to an ontological databank 118.

FIG. 1 is merely an example, which should not unduly limit the scope of the claims herein. It is to be understood that the specific designation for the network environment 100 is provided as an example and is not to be construed as limiting the network environment 100 to specific numbers, types, or arrangements of server arrangements, client devices, data communication networks and ontological databanks. A person skilled in the art will recognize many variations, alternatives, and modifications of embodiments of the present disclosure.

Figure 2:
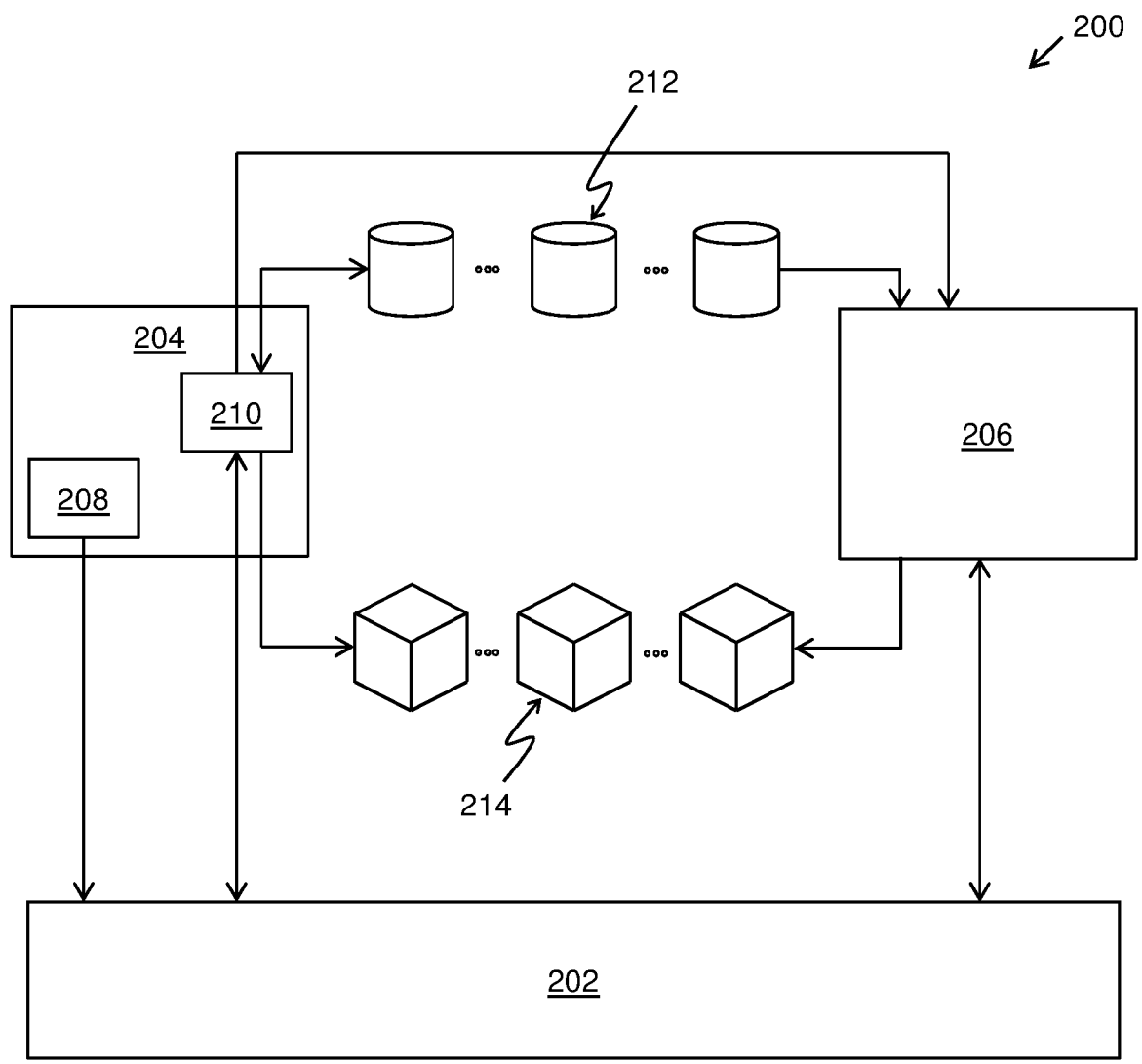
FIG. 2 is a schematic illustration of a high-level architecture of a network environment in which a system for executing a document access transaction is implemented, pursuant to a specific embodiment of the present disclosure.

FIG. 2 is a schematic illustration of a high-level architecture of a network environment 200 in which a system for executing a document access transaction is implemented, pursuant to a specific embodiment of the present disclosure.

The network environment 200 comprises a server arrangement 202 including one or more processors, a first client device 204 and a second client device 206. The server arrangement 202 is communicably coupled via one or more data communication networks (not shown) with the first client device 204 and the second client device 206. As shown, the first client device 204 comprises a remote extraction module 208 and a data sharing module 210.

With reference to FIG. 2, the network environment 200 comprises a distributed file system 212 and a blockchain platform 214.

The remote extraction module 208 is configured to transmit value features extracted from a document and metainformation pertaining to the document to the server arrangement 202. The server arrangement 202 is configured to perform various operations, for example, as described earlier.

The document sharing module 210 is configured to encrypt the document and store the encrypted document in the distributed file system 212. The distributed file system 212 is operable to generate a hash that uniquely identifies the document and communicate the hash to the document sharing module 210.

The document sharing module 210 is configured to store the hash of the document on the blockchain platform 214, wherein the blockchain platform 214 associates a timestamp with the hash of the document. Moreover, the document sharing module 210 is configured to communicate the hash of the document to the server arrangement 202.

The server arrangement 202 is configured to communicate the hash of the document to the second client device 206, for example, upon receipt of a request for accessing the document from the second client device 206, or upon successful validation of the request. This enables the second client device 206 to retrieve the encrypted document from the distributed file system 212.

The document sharing module 210 is configured to communicate to the second client device 206 a key to be used to decrypt the encrypted document, upon successful validation of the request for accessing the document. This enables the second client device 206 to decrypt the encrypted document using the key.

In some implementations, the second client device 206 makes a payment transaction for purchasing the document using the blockchain platform 214.

FIG. 2 is merely an example, which should not unduly limit the scope of the claims herein. It is to be understood that the specific designation for the network environment 200 is provided as an example and is not to be construed as limiting the network environment 200 to specific numbers, types, or arrangements of server arrangements, client devices, modules, distributed file systems and blockchain platforms. A person skilled in the art will recognize many variations, alternatives, and modifications of embodiments of the present disclosure.

Figure 3A:
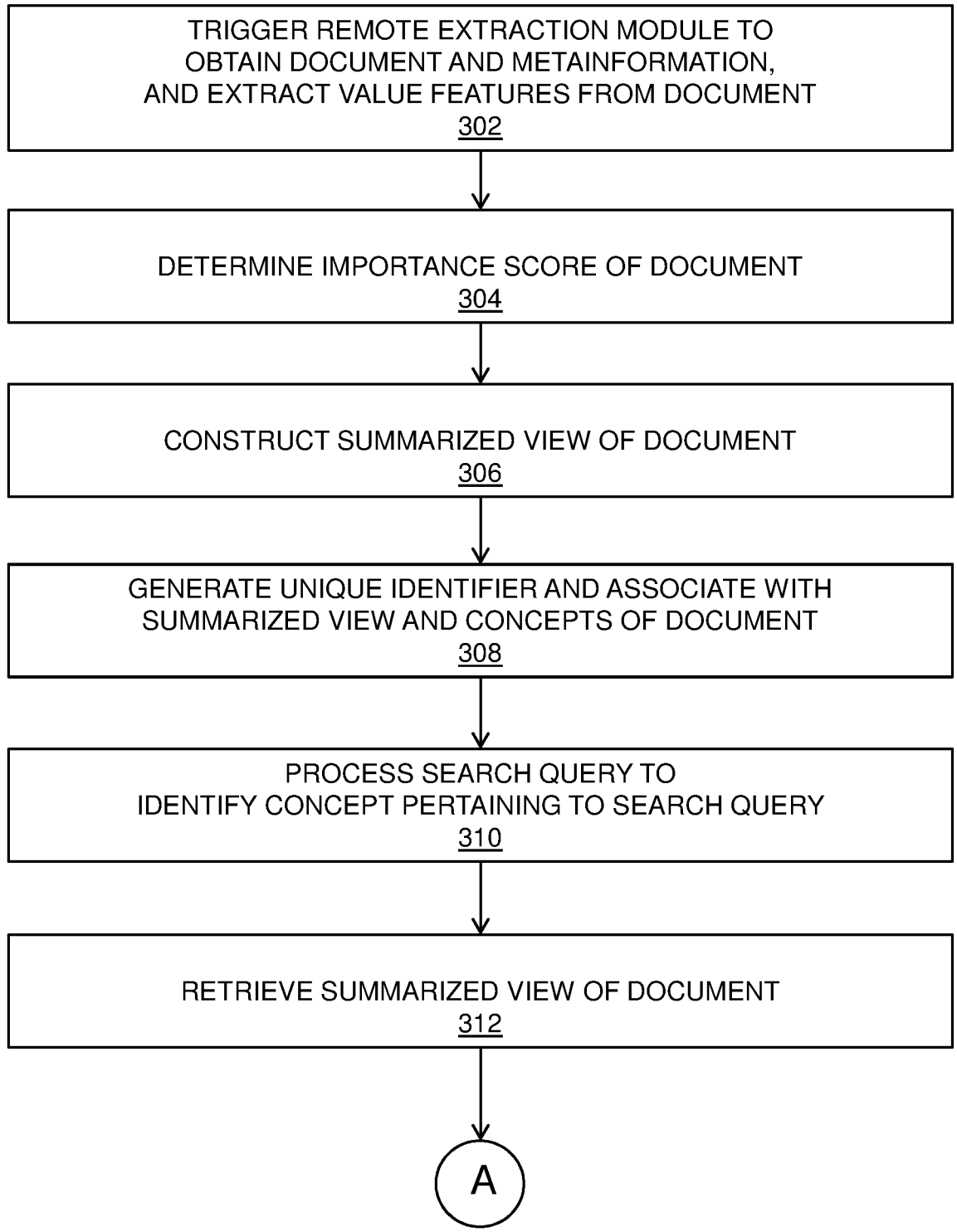
FIGS. 3A and 3B collectively are a flow chart depicting steps of a method for executing a document access transaction, in accordance with an embodiment of the present disclosure.
Figure 3B:
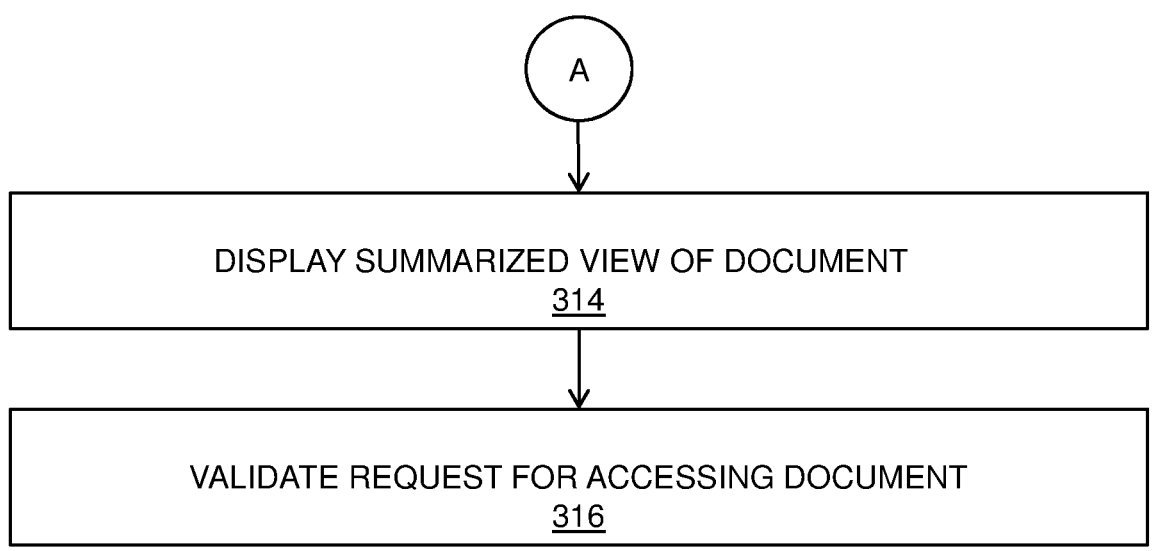

Referring to FIGS. 3A and 3B, illustrated is a flow chart depicting steps of a method for executing a document access transaction, in accordance with an embodiment of the present disclosure. The method is depicted as a collection of steps in a logical flow diagram, which represents a sequence of steps that can be implemented in hardware, software, or a combination thereof, for example as aforementioned.

The method is implemented via a system comprising a server arrangement including one or more processors, the server arrangement being communicably coupled via one or more data communication networks with a first client device and a second client device.

At a step 302, a remote extraction module, stored on the first client device, is triggered to obtain a document and metainformation pertaining to the document, extract one or more value features from the document based on an identification of one or more concepts of the document that are identified as associated with concepts stored in an ontological databank, the ontological databank being communicably coupled to the remote extraction module, and transmit the one or more value features and the metainformation to the server arrangement.

At a step 304, an importance score of the document is determined, using a scoring module of the server arrangement, based on the one or more value features and the metainformation pertaining to the document.

At a step 306, a summarized view of the document is constructed based on at least one of: the one or more value features, the metainformation, the one or more concepts of the document and the importance score.

At a step 308, a persistence module of the server arrangement is initialized to generate a unique identifier for the document and associate the unique identifier with the summarized view and with the one or more concepts of the document.

At a step 310, a search query, received from the second client device, is processed to identify at least one concept pertaining to the search query.

At a step 312, the summarized view of the document is retrieved based on the unique identifier of the document, when the at least one concept pertaining to the search query matches at least one of the one or more concepts of the document.

At a step 314, the summarized view of the document is displayed on a user interface of the second client device.

At a step 316, a request, received from the second client device, for accessing the document is validated using a validation module of the server arrangement. The validation module is configured to cause the first client device to allow the second client device to access the document, when the request is validated successfully.

The steps 302 to 316 are only illustrative and other alternatives can also be provided where one or more steps are added, one or more steps are removed, or one or more steps are provided in a different sequence without departing from the scope of the claims herein.

FIGS. 4A and 4B are example views of a graphical user interface that are presented to a first user of a first client device, in accordance with an embodiment of the present disclosure. The graphical user interface allows the first user to submit to, a remote extraction module stored on the first client device, a document and metainformation pertaining to the document.

With reference to FIG. 4A, a first example view includes text boxes and/or drop-down menus that allow the first user to enter details and/or select a suitable option.

With reference to FIG. 4B, a second example view allows the first user to select one or more documents for submission.

FIGS. 4A and 4B are merely examples, which should not unduly limit the scope of the claims herein. A person skilled in the art will recognize many variations, alternatives, and modifications of embodiments of the present disclosure. For example, another example view of the graphical user interface can show and allow the first user to edit the metainformation provided by the user.

Figure 5A:

FIGS. 5A and 5B are example views of a graphical user interface that are presented to a second user of a second client device, in accordance with an embodiment of the present disclosure. The graphical user interface allows the second user to input a search query and access a document.

With reference to FIG. 5A, a first example view includes an input field for the search query. Subsequent to an input of the search query by the second user, a list of documents related to the search query is shown.

With reference to FIG. 5B, a second example view presents a summarized view of a document, for example, based upon a user's selection from the list of documents.

FIGS. 5A and 5B are merely examples, which should not unduly limit the scope of the claims herein. A person skilled in the art will recognize many variations, alternatives, and modifications of embodiments of the present disclosure. For example, another example view of the graphical user interface can allow the second user to initiate a request for accessing the document.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

What is claimed is:

1. A system for access transaction of a document containing sensitive and confidential information, the system comprising a server arrangement including one or more processors, the server arrangement being communicably coupled via one or more data communication networks with a first client device and a second client device, wherein the server arrangement, when operated, provides a platform configured to:

receive an access request for a document selected, by the second user, from a list of documents retrieved in response to a search query and displayed, on a user interface connected to the second client device, wherein each of the document in the list is associated with a summarized view and an importance score, and wherein the importance score, displayed along-with the summarized view, for each of the document in the list is determined on the platform without accessing and storing, on the platform, any document of said list of documents, wherein the importance score is determined, by a scoring module on the server arrangement, based on metainformation of the document and one or more value features transmitted to the server arrangement by a remote sharing module of the first client device submitting the document, wherein the one or more value features of the document comprise information elements related to entities and semantic inter-relationships between the entities, wherein the importance score is indicative of technical importance of the document, and wherein the metainformation of the document comprises information related to a statistical significance of current research work related to the document;

validate the access request for the document by the second user;

retrieve and deliver to the second client device a hash pertaining to the document wherein the hash corresponds to a location of the document in a distributed file storage system; and cause the first client device to communicate the document to the second client device in response to a successful validation of the access request.

2. The system of claim 1, wherein the search query is expanded, based on an ontological databank, to include one or more concepts from the ontological databank and wherein each of the document in the list of all documents correspond to at least one concept of the ontological databank.

3. The system of claim 1, wherein the remote extraction module is operable to extract the one or more value features based on an ontological databank related to a technical field of the document, the ontological databank being communicably coupled to the remote extraction module.

4. The system of claim 1, wherein the summarized views are constructed, on the fly, at the time of processing the search query.

5. The system of claim 1, wherein the summarized views are pre stored on the server arrangement.

6. The system of claim 1, wherein the document is stored on the distributed file storage system by a document sharing module of the first client device.

7. The system of claim 6, wherein the document sharing module is configured to encrypt the document with a key, prior to storing on the distributed file storage system, and communicate the key to the second client device in response to successful validation of the access request.

8. The system of claim 6, wherein the document sharing module is configured to store the hash of the document on a blockchain platform, wherein the blockchain platform associates a timestamp with the hash of the document.

9. A method for access transaction of a document containing sensitive and confidential information, wherein the method is implemented via a system comprising a server arrangement including one or more processors, the server arrangement being communicably coupled via one or more data communication networks with a first client device and a second client device, the method comprising:

receive an access request for a document selected, by the second user, from a list of documents retrieved in response to a search query and displayed, on a user interface connected to the second client device, wherein each of the document in the list is associated with a summarized view and an importance score, and wherein the importance score, displayed along-with the summarized view, for each of the document in the list is determined on the platform without accessing and storing, on the platform, any document of said list of documents, wherein the importance score is determined, by a scoring module on the server arrangement, based on metainformation of the document and one or more value features transmitted to the server arrangement by a remote sharing module of the first client device submitting the document, wherein the one or more value features of the document comprise information elements related to entities and semantic inter-relationships between the entities, wherein the importance score is indicative of technical importance of the document, and wherein the metainformation of the document comprises information related to a statistical significance of current research work related to the document;

validating the access request for the document by the second user;

retrieving and delivering to the second client device a hash pertaining to the document wherein the hash corresponds to a location of the document in a distributed file storage system; and causing the first client device to communicate the document to the second client device in response to a successful validation of the access request.

10. The method of claim 9, wherein the search query is expanded, based on an ontological databank, to include one or more concepts from the ontological databank and wherein each of the document in the list of all documents correspond to at least one concept of the ontological databank.

11. The method of claim 9, wherein the remote extraction module is operable to extract the one or more value features based on an ontological databank related to a technical field of the document, the ontological databank being communicably coupled to the remote extraction module.

12. The method of claim 9, wherein the summarized views are constructed, on the fly, at the time of processing the search query.

13. The method of claim 9, wherein the summarized views are prestored on the server arrangement.

14. The method of claim 9, wherein the document is stored on the distributed storage system by a document sharing module of the first client device.

15. The method of claim 14, wherein the document sharing module is configured to encrypt the document with a key, prior to storing on the distributed file storage system, and communicate the key to the second client device in response to successful validation of the access request.

16. The method of claim 14, wherein the document sharing module is configured to store the hash of the document on a blockchain platform, wherein the blockchain platform associates a timestamp with the hash of the document.

* * * * *